(12) United States Patent
Kröning et al.

(10) Patent No.: US 7,926,350 B2
(45) Date of Patent: Apr. 19, 2011

(54) METHOD FOR THE NON-DESTRUCTIVE INSPECTION OF A TEST BODY USING ULTRASOUND

(75) Inventors: Michael Kröning, Saarbrücken (DE); Andrey Bulavinov, Saarbrücken (DE); Krishna Mohan Reddy, Saarbrücken (DE); Ludwig Von Bernus, Windsbach (DE)

(73) Assignee: Fraunhofer-Gesellschaft zur Förderung der Angewandten Forschung E.V., Munich (DE)

( * ) Notice: Subject to any disclaimer, the term of this patent is extended or adjusted under 35 U.S.C. 154(b) by 308 days.

(21) Appl. No.: 12/091,815

(22) PCT Filed: Jun. 21, 2006

(86) PCT No.: PCT/EP2006/005931
§ 371 (c)(1),
(2), (4) Date: Nov. 19, 2008

(87) PCT Pub. No.: WO2007/048454
PCT Pub. Date: May 3, 2007

(65) Prior Publication Data
US 2009/0178484 A1 Jul. 16, 2009

(30) Foreign Application Priority Data
Oct. 28, 2005 (DE) .......... 10 2005 051 781

(51) Int. Cl.
*G01N 29/04* (2006.01)
*A61B 8/00* (2006.01)

(52) U.S. Cl. ........... 73/598; 73/602; 73/606; 73/627; 600/437; 600/440

(58) Field of Classification Search ............ 73/598, 73/602, 606, 625, 626, 627; 600/437, 447, 600/459; 702/39
See application file for complete search history.

(56) References Cited

U.S. PATENT DOCUMENTS

| | | | |
|---|---|---|---|
| 5,005,418 A | 4/1991 | Anderson | |
| 5,269,309 A * | 12/1993 | Fort et al. | 600/447 |
| 5,465,722 A * | 11/1995 | Fort et al. | 600/447 |
| 5,601,083 A | 2/1997 | Anderson | |
| 6,540,678 B2 * | 4/2003 | Rather et al. | 600/437 |
| 6,685,645 B1 | 2/2004 | McLaughlin et al. | |
| 2010/0106431 A1* | 4/2010 | Baba et al. | 702/39 |
| 2010/0234729 A1* | 9/2010 | Bae et al. | 600/441 |
| 2010/0274136 A1* | 10/2010 | Cerofolini | 600/459 |

FOREIGN PATENT DOCUMENTS

EP 1 300 690 A1 4/2003
WO WO 2004/005957 A1 1/2004

* cited by examiner

*Primary Examiner* — Jacques M Saint Surin
(74) *Attorney, Agent, or Firm* — Antonelli, Terry, Stout & Kraus, LLP.

(57) ABSTRACT

A method for the non-destructive inspection of a test body using ultrasound is disclosed, in which at least one ultrasonic transducer couples ultrasonic waves into the test body and ultrasonic waves reflected inside the test body are received by ultrasonic transducers and converted into ultrasonic signals, which form the basis of the non-destructive inspection.

12 Claims, 4 Drawing Sheets a)      b)

c)

a)        b)        c)

METHOD FOR THE NON-DESTRUCTIVE INSPECTION OF A TEST BODY USING ULTRASOUND

BACKGROUND OF THE INVENTION

1. Field of the Invention

The present invention relates to a method for the non-destructive inspection of a test body using ultrasound, in which ultrasonic waves are coupled into the test body by means of a multiplicity of ultrasonic transducers and the ultrasonic waves reflected inside the test body are received by a multiplicity of ultrasonic transducers and converted into ultrasonic signals, which form the basis of the non-destructive inspection.

2. Description of the Prior Art

The manner of proceeding in non-destructive inspection of a test body by means of ultrasound, and for the purpose of inspecting material for flaws in the material, such as cracks, inclusions or other inhomogeneities in the material comprises coupling ultrasonic waves into the test body, detecting the ultrasonic waves transmitted through or reflected, bent, scattered and/or broken inside the test body as well as evaluating the ultrasonic waves converted into ultrasonic signals.

Using the above as such state-of-the-art methods of inspection, it is possible to detect and evaluate the ultrasonic-wave transmission properties, and reflection properties, of a test body. In this method, which originally stemmed from medical technology (ultrasonic diagnostics), faulty sites, such as cracks in the materials, inclusions or seams in a test body are imaged by means of corresponding evaluation of the received ultrasonic signals as areas with altered reflection properties. Position, shape and size of the faulty sites can be depicted three-dimensionally in a spatially highly resolved manner.

Obviously, the fields of application of this method are evident. Mentioned as examples are application of the method for inspection, examination and detection of the homogeneity properties or solidity properties of the structural parts of buildings (concrete walls, ceiling elements or wall elements, etc.) or crack inspection, for example in railroad wagon wheels or airplane parts.

Employed in many applications of non-destructive material inspection using ultrasound are a multiplicity of ultrasound transducers which are combined for better handling into a so-called ultrasonic probe or emitter array probe. Fundamentally, two types of ultrasonic probes are differentiated. It is called an impulse-echo probe if the probe couples an ultrasonic-wave package into the test body and the ultrasonic waves reflected in the test body are received again by the probe. On the other hand, probes with separate ultrasonic transducers for coupling to and receivers for receiving ultrasonic waves are called transmission/reception probes.

In all the state-of-the-art ultrasonic probes, the single ultrasonic transducers are each connected to a control device which is provided with a separate control electronics, that is an electric control channel, for each ultrasonic transducer with single ultrasonic transducers triggered independently of each other and function, for example, as a ultrasonic transmitter or as a ultrasonic receiver. In particular, such separate triggering allows operating the single ultrasonic transducers with a different phase position and a different amplitude. FIG. 2 shows schematically a state-of-the-art setup of an emitter array system which, using phased array technology, is able to excite ultrasonic waves in the probe at any angle and in any focusing range and to receive the same therefrom. The emitter array system comprises a probe 1 with a multiplicity of single ultrasonic transducers which are all connected to a multi-channel electronic via a cable 2 to transmit electric signals. For each channel, the ultrasonic electronics triggering an ultrasonic transducer is provided with an amplifier 3, an analog/digital converter 4, transmission/reception delay elements 5, a signal adder 6 and a sector image reconstruction unit 7.

In order to carry out a measurement with which the transmission capacity of a probe is to be tested, the control device excites at least one usually, however, a multiplicity of ultrasonic transducers of the emitter array probe may couple ultrasonic waves into the test body for a brief, limited time interval. The resulting ultrasonic wave packages which are inputted are reflected, for example, at faulty sites inside the test body and return as reflected ultrasonic waves to the ultrasonic transducers now operating as receivers and are converted into ultrasonic signals by the receivers and conveyed to the control device for evaluation. The time period between emission and reception of the ultrasonic signals is usually referred to as a measurement cycle. Last but not least, for improved signal detection and evaluation, a multiplicity of such type measurement cycles are carried out successively to obtain an acceptable signal/noise ratio.

In many applications, the goal is to detect inside the test body volume in a finely as possible resolved manner the transmission properties and reflection properties of a test body. For this purpose, the time delay of the transmission cycles is correspondingly adjusted to set the irradiation direction and the focusing depth. The received ultrasonic signals of the single ultrasonic transducers of the emitter array probe are so to say added to the phase delay so that in a transmission cycle an ultrasonic signal is generated for an irradiation angle and, if need be, for a certain focusing depth. This is referred to as a so-called A-image, which is shown in FIG. 3a. The A-image represents the ultrasonic echo along a given "view propagation direction, and a sound propagation direction" through the test body. It can be viewed as a 1-dimensional sectional image like an intersecting line through the test body along which ultrasonic echo signals are shown locally resolved. Sound transmission through the test body at different angles (that is the sonic bundle is pivoted in the test body, preferably within a uniform pivoting plane) permits reconstructing a so-called sector image, which is composed of a multiplicity of single A-images as the graph according to FIG. 3b shows. Additionally, the single echo signals in different colors along the multiplicity of combined A-images yields an interpretable sector image or an interpretable B-image according to the image representation in FIG. 3c, showing sites of increased reflectivity in a cutting plane or a sector inside the test body.

A drawback in using the phased array method for the non-destructive inspection of the material of a test body is however that a great deal of time and measuring effort is required until a test body is inspected as thoroughly as possible as the aim is to obtain sufficiently reliable measuring signals from, if possible, all the regions of the volume for complete signal evaluation. Thus, in one measurement cycle or in a multiplicity of measurement cycles with the same phase triggering of the ultrasonic transducers, only limited information is obtained about the reflection properties in only one volume region or along one given sector of the test body. A very large number of measurements each with different phase triggering is therefore needed to examine the entire test body volume, thus requiring a great amount of time to carry out complete material inspection. Time consuming and work intensive reprogramming is required to set a new irradiation angle, respectively a new focal position.

Another disadvantage is that a given irradiation angle determines the probe aperture, that is, it is not possible to select the aperture optimally for all irradiation angles, which impairs the resolution of the measurements.

A further disadvantage of the phased array method is that for each ultrasonic transducer, a transmission channel and reception channel has to be provided with corresponding electronics connected via electrical connections to the respective ultrasonic transducer. As presently employed ultrasonic probes usually comprise 16 or more ultrasonic transducers, the connections between the probe and the control device usually require a thick, inflexible and therefore difficult to handle cable.

To remedy the abovementioned problems, DE 10 2004 059 856.8-52 describes the principle of a clocked emitter array system in which all the ultrasonic transducers of the emitter array probe are successively excited, whereby in each transmission cycle all the ultrasonic transducers receive the ultrasonic echo signals returning from the test body. The received time signals are stored, and the stored time signals are not evaluated based on a reconstruction algorithm until after termination of the sound transmission through the test body. In this manner, it is possible to reconstruct the ultrasonic signals of one or a multiplicity of irradiation directions, and of focusing depths, from the stored time signals.

SUMMARY OF THE INVENTION

The present invention permits further improvement even regarding the emitter array system described in the aforecited DE 10 2004 059 856.8-52 as to time consumption and work intensity for carrying out non-destructive inspection of a test body. In particular, the time required to inspect such types of test bodies should be reduced decisively.

The method according to the invention utilizes special physical wave propagation phenomena in combination with a special reconstruction technique permitting obtaining reconstruction of single time-resolved and locally resolved ultrasonic echo signals along a given irradiation angle, (so-called A-images) including sector images in the form of two-dimensional ultrasonic sectional images as well as three-dimensional volumetric images without multiple transmission and reception, that is, solely within a single transmission cycle.

According to the invention, a method for the non-destructive inspection of a test body using ultrasound is distinguished by an ultrasonic transducer being provided on a surface of a test body and activated in a first step in such a manner that the ultrasonic waves coupled into the test body propagate largely uniformly spatially distributed inside the test body. In a next step, the ultrasonic waves reflected inside the test body are received with a multiplicity m of ultrasonic transducers provided on the surface of the test body. Each ultrasonic transducer generates ultrasonic time signals containing time-resolved amplitude information. All of the ultrasonic time signals received by m ultrasonic transducers are stored in a memory unit for subsequent processing and evaluation. Based on the m ultrasonic time signals, a 3-dimensional volumetric image, a sector image in the form of a 2-dimensional ultrasonic sectional image through the test body or an A-image in the form of a one-dimensional image along a given irradiation angle, is finally determined by means of a reconstruction algorithm.

Suited for carrying out the method according to the invention is a state-of-the-art emitter array probe with a multiplicity of array-like, that is, linearly or matrix-like disposed ultrasonic transducers, which all have as small as possible dimensions in the longitudinal direction to the test body surface and due to this or apart from this possess a very wide directional characteristic. That is each single ultrasonic transducer is fundamentally able to provide ultrasonic waves into all reachable spatial directions inside the test body on whose surface the ultrasonic transducer is positioned for the purpose of acoustic coupling.

If a single ultrasonic transducer of the emitter array probe is now excited by means of an electrical impulse, the ultrasonic waves excited in the test body material propagate in all the spatial directions accessible inside the test body, preferably with a spherical propagation characteristic. If there is material incompleteness in the test body volume, which appear as reflectors, these material incompletenesses become sources of secondary ultrasonic waves which are received as reflected parts of ultrasonic waves by the multiplicity m of the ultrasonic transducers inside the emitter array probe.

Alternatively for emitting ultrasonic waves by means of a single ultrasonic transducer, according to the invention it is also as possible to provide a multiplicity n of array-like distributed ultrasonic transducers disposed on a surface of the test body, of which at least one group of i of the n ultrasonic transducers are activated in such a manner that the i ultrasonic wave fronts coupled into the test body superimpose to form an overall wave front propagating largely in a uniformly spatially distributed manner. For the numerical parameter i is given: $3 \leq i \leq n$. For formation of a spatially largely uniformly distributed overall front wave, the single i ultrasonic transducers are activated in a time-delayed manner with corresponding electrical emission impulses in such a manner that the wave front forming inside the test body is as cylindrical or spherical as possible, thereby ensuring that sound propagation, similar to the alternative solution described in the preceding, occurs largely uniformly in all irradiation directions during a transmission cycle.

Similarly, as in the aforedescribed alternative embodiment, parts of the ultrasonic waves reflected back are received by a multiplicity m of ultrasonic transducers provided on the surface utilizing the sound emission via a multiplicity i of single transducers inside the test body, with the multiplicity m preferably corresponding to the entirety of all ultrasonic transducers contained inside an emitter array probe and preferably m=n. The n provided ultrasonic transducers generate correspondingly m ultrasonic time signals in which time-resolved amplitude information is contained which is stored in the corresponding manner for further reconstruction evaluation.

Contrary to the hitherto applied reconstruction methods, in which a construction of two-dimensional sector images, and B-images, is carried out based on the compilation of a multiplicity of single A-images, each representing ultrasonic signals along a defined irradiation angle, and an "observation angle", the reconstruction method of the invention is based on taking into consideration the duration of the ultrasound starting with the transmission to each single spatial point inside the test body and returning to the site of one ultrasonic transducer which receives part of the reflected ultrasonic wave. In this manner, it is possible to reconstruct the position of a volumetric image or a sector image without calculating single A-images. But rather, based on the received ultrasonic time signals, the volume of the test body is subdivided into single spatial points, so-called voxels, to each of which at least one part of the ultrasonic echo signal coming from the respective spatial point is assigned, which corresponds to a so-called voxel value. Depending on certain predefined evaluation focal points, for compilation of, for example, a B-image, and of a sector image, all those voxels are selected from the entirety of all the stored voxel values contained in the given section plane. Thus, a two-dimensional sector image is composed pixel-wise of a multiplicity of single voxel values and not as before by combining single calculated A-images.

Detection and storing of the voxel values representing all of the to-be-inspected test body volume permits conducting, depending on the purpose of the inspection, as many test body inspections as desired by means of one non-destructive ultrasonic inspection without requiring investing a great deal of time or money. Further aspects regarding the variants of the method according to the solution can be drawn from the further description with reference to the preferred embodiments.

BRIEF DESCRIPTION OF THE DRAWINGS

The present invention is made more apparent in the following, without the intention of limiting the scope or spirit of the inventive idea, using preferred embodiments with reference to the accompanying drawings.

DESCRIPTION OF THE INVENTION

Figure 1:
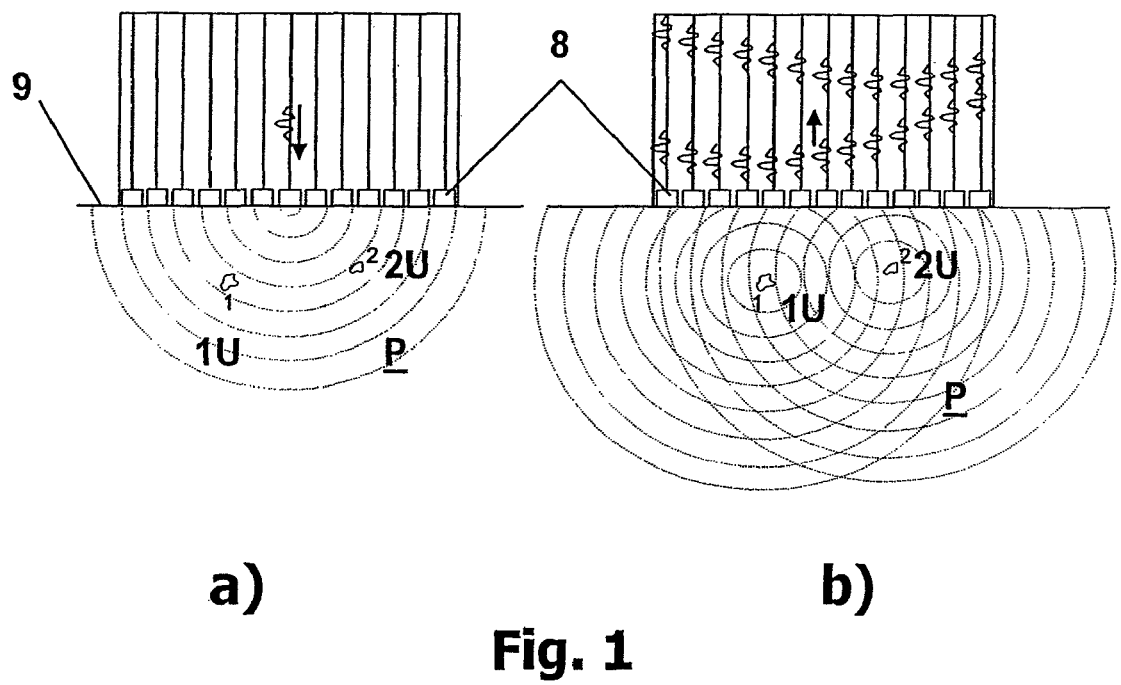
FIGS. 1a-c show transmission and reception sequences for carrying out an ultrasonic inspection in a test body.
Figure 1:
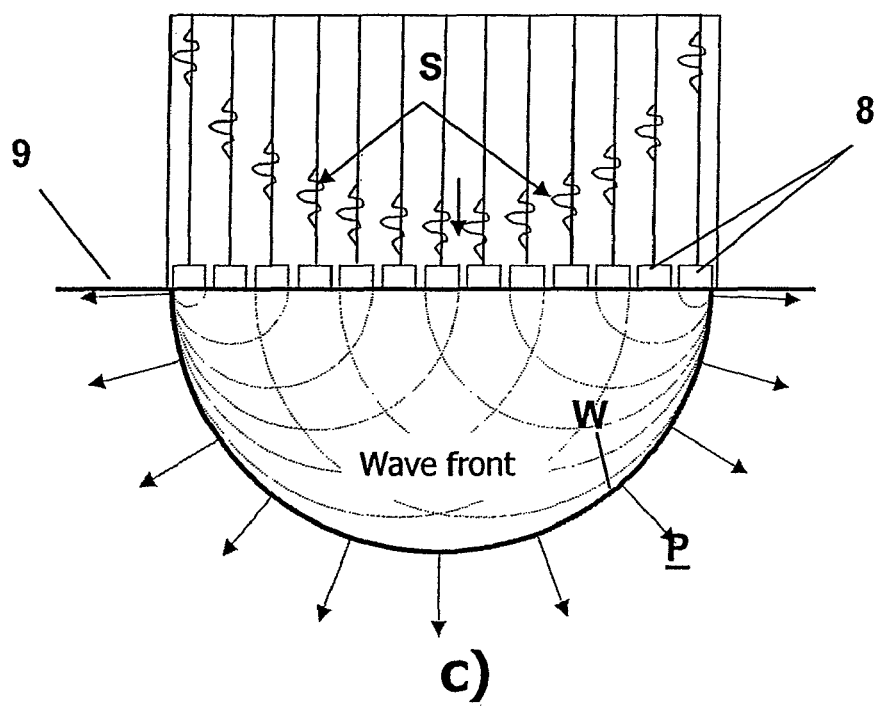

FIG. 1a shows a schematic of an emitter array probe provided with a multiplicity n of linearly adjacent arranged ultrasonic transducers 8 which are disposed along the surface 9 of a test body P.

The single transducers 8 are distinguished by very small dimensions lateral to the surface 9 of the test body P and have a very wide directional characteristic. In this case if the ultrasonic transducers 8 of the emitter array probe were all excited at the same time, due to the aperture/wavelength ratio, they would form an aligned sound field penetrating the test body P.

The method according to the invention, on the other hand, utilizes the capacity of a single ultrasonic transducer 8, which preferably is disposed centered inside the emitter array group probe and which, due to its wide directional characteristic with corresponding electrical excitation, is able to cover all the irradiation directions inside the body. With selective excitation of a single ultrasonic transducer with pulsed excitation, spherically formed wave fronts are irradiated into the inside of the test body P as shown in the representation according to FIG. 1a. It is assumed that inside the test body P two material incompletenesses 1U and 2U are provided at which the ultrasonic waves are partially reflected. FIG. 1b shows the reception situation in which the secondary ultrasonic waves emitting from the material incompletenesses 1U and 2U are received by the multiplicity m of ultrasonic transducers 8 provided on the surface of the test body. The back-reflected ultrasonic waves received by the ultrasonic transducers 8 correspond to echo signals in which amplitude information and duration information regarding the material incompletenesses 1U and 2U inside the test body P are contained. However, the sites of the material incompletenesses can at first not be located. The echo signals received by the ultrasonic transducers 8 undergo corresponding amplification, filtering and digitalization and are ultimately stored in digital form in a memory.

A special advantage regarding the transmission/reception process shown in FIGS. 1a and 1b that must be pointed out is that no expensive transmission delays are required for the producing of the triggering of the multiplicity of single ultrasonic transducers. This is an advantage which is positively reflected in the component costs required in the realization of such a type system.

Although the advantage described in the preceding does not apply to the alternative transmission and reception arrangement shown in FIG. 1c, the emitter array probe depicted in FIG. 1c is also able to generate in the same manner an overall wave front propagating spherically inside the test body, which is a prerequisite with which simplified evaluation of the ultrasonic signals becomes possible as the further preferred embodiments will demonstrate.

Contrary to the transmission process shown and described in FIG. 1a, the multiplicity of the ultrasonic transducers disposed on the surface 9 of the test body P according to the preferred embodiment in FIG. 1c is excited with a correspondingly set transmission delay by the electrical transmission impulses S so that the wave front W forming in the test body P assumes a spherical shape, thereby also ensuring sound propagation in all irradiation directions within a transmission cycle. In this case, the receiving process also corresponds to the situation described with reference to FIG. 1b, whereby in the present case the digitalized ultrasonic signals, and echo signals, are stored in a memory taking into consideration the amplitude information and duration information assignable to them.

Figure 2:
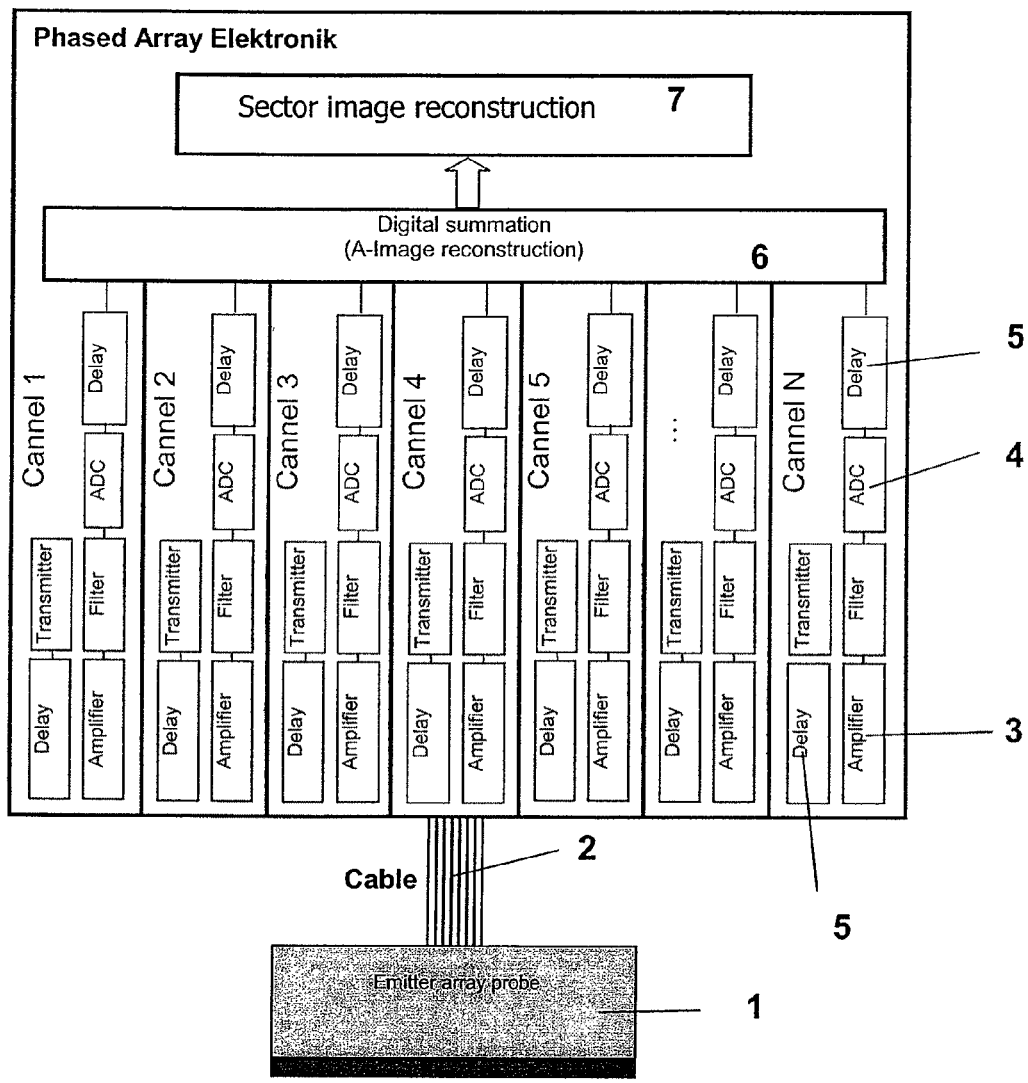
FIG. 2 shows a schematic setup of a state-of-the art emitter array system.
Figure 3:
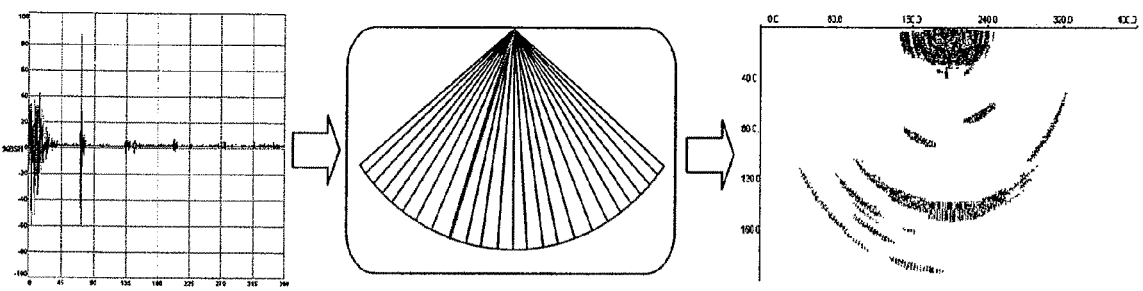
FIGS. 3a-c show a representation of a reconstruction of a sector image, and of a B-image.
Figure 4:
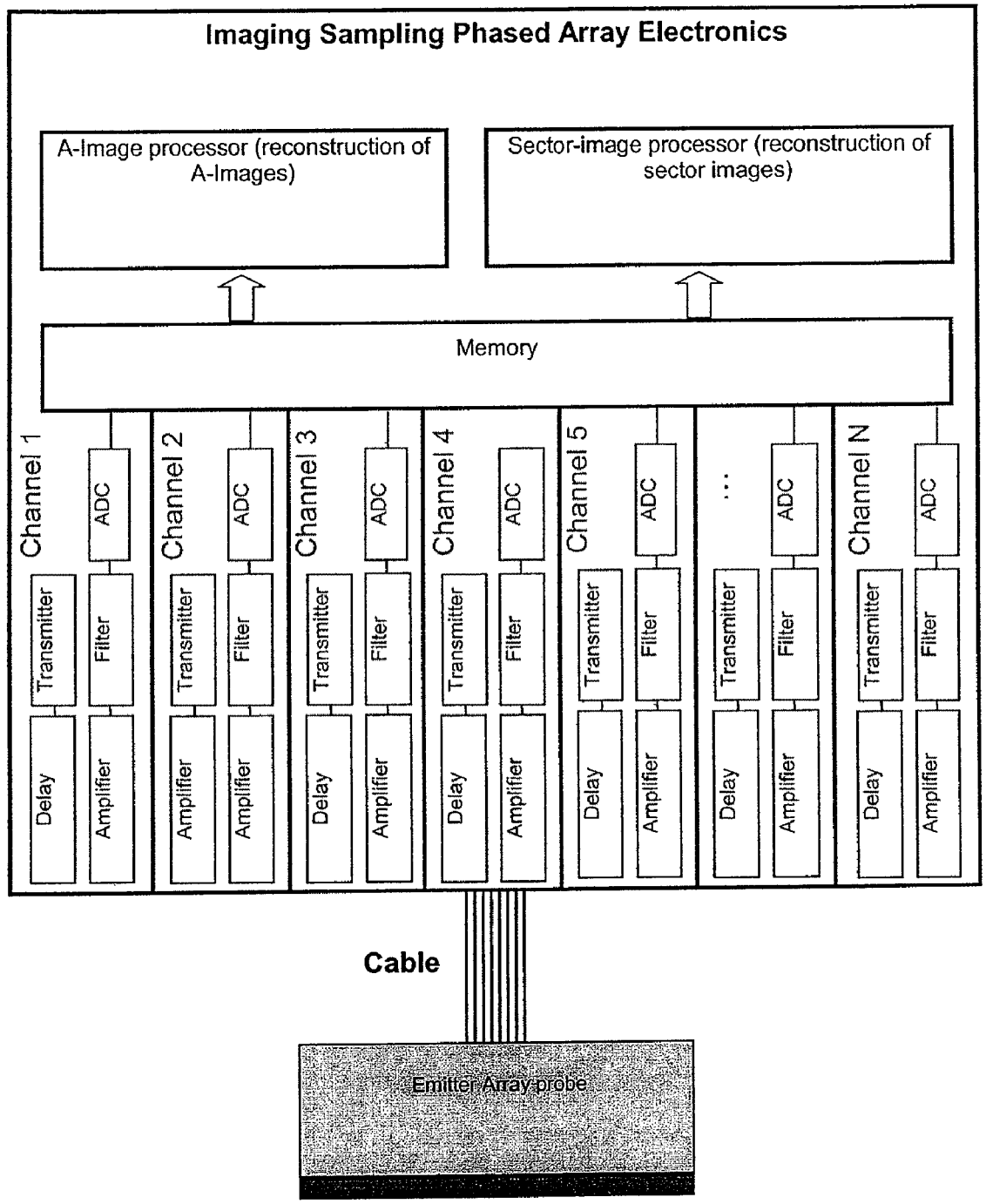
FIG. 4 shows the setup of a modified emitter array system.
Figure 5:
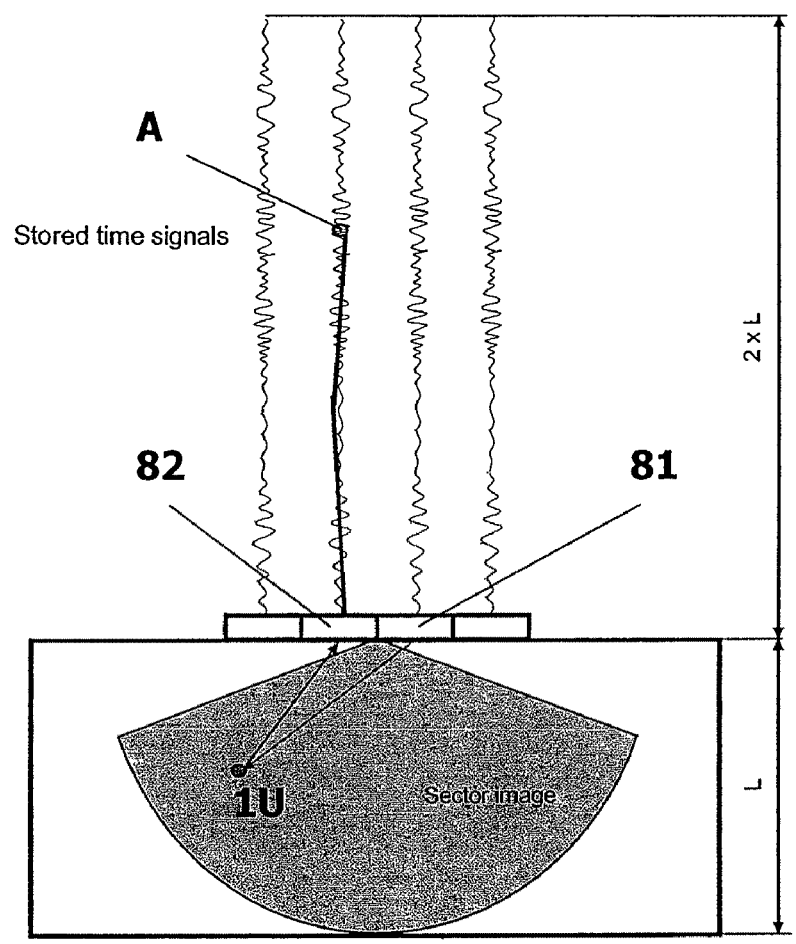
FIG. 5 shows a representation of a reconstruction of a sector image, and a D-image.

In order to carry out the transmission and reception scenarios described in the preceding, a modified emitter array probe, depicted schematically in FIG. 4, is placed on the surface 9 of a test body P. Contrary to the state-of-the-art emitter array probe shown according to FIG. 2, no time delay element 5 is required inside the reception logic, but rather the amplified, filtered and digitally converted echo signals are stored in a memory retaining the amplitude information and the time information. The information required for representation of the A-images or the B-images, the sector images, is computed by means of special reconstruction units directly from the stored echo signals. The main concept of forming the basis of the reconstruction is based on accounting for the ultrasound duration from each single ultrasonic transmission site to each spatial point inside the test body as well as back to each site at which an ultrasonic receiver is provided. In other words the entire spatial area of the test body is subdivided into very small single volumetric areas, so-called voxels. Within the transmission cycle an ultrasonic echo information is assignable to each single voxel. This ultrasonic echo information is stored as digital time and amplitude information in a memory unit. In order to reconstruct for example a B-image, and a sector image, it is necessary to select from the entirety of all the stored voxel values those lying in an cutting plane through the test body to be inspected. This process is depicted schematically in FIG. 5. Thus, for example, it is assumed that an ultrasonic wave is emitted by the ultrasonic emitter 81 into the inside of the test body P, which is reflected at the material incompleteness 1U and is received by the ultrasonic transducer 82. Due to a measurement of duration and amplitude value detection, a specific amplitude value A can be assigned to the material incompleteness 1U inside the test body P and is stored in a corresponding manner. It is easy to follow that in this manner corresponding amplitude information can be assigned time-resolved to each single spatial point inside the test body P. If the goal is to detect a particular sector image or B-image, it is only necessary to select single stored voxel values whose combination yields a two-dimensional sectional image through the test body.

Figure 6:
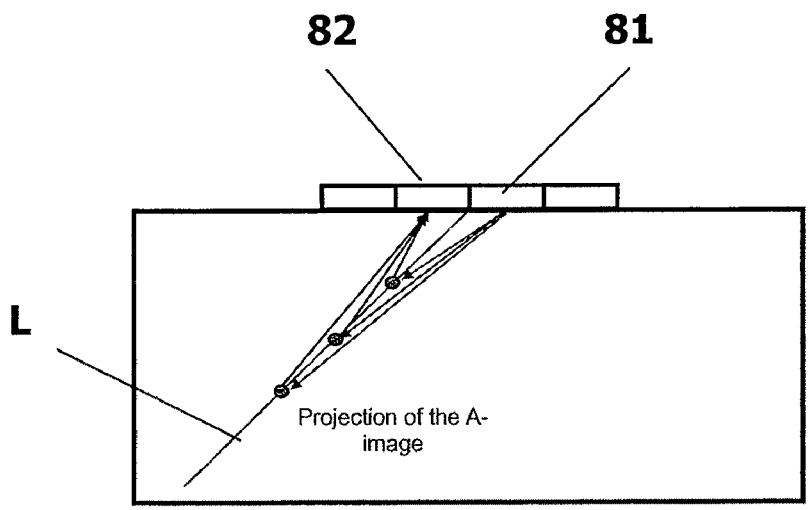
FIG. 6 shows reconstruction of an A-image.

On the other hand, if it is desired to generate a conventional A-image in order, for example, to represent the ultrasonic signal at a certain irradiation angle in the test body P, such a one-dimensional sectional image can also be reconstructed from the stored information. According to the schematic representation in FIG. 6, in order to reconstruct an A-image, contrary to reconstructing a B-image, all the reconstructed voxel values lie along a straight line L in such a manner that a one-dimensional projection of an A-image is obtained.

In this manner, a comprehensive set of data can be obtained within a single transmission cycle from which both complete sector images as well as single A-images can be reconstructed for any irradiation angle. A prerequisite therefor is using an emitter array system set up according to the phased array system. In the same manner, volumetric images can, of course, also be generated directly from the stored set of data by means of corresponding viewing together of the spatially distributed voxel values.

Duration-related reconstruction yields focusing effects, with the focusing point lying in each single voxel of the sector image, and of the generated A-image. Such a synthetic focusing method also helps improve considerably sensitivity, lateral resolution and the signal-to-noise ratio of the conducted ultrasonic inspection. If the same signal and image quality, for example using conventional emitter array technology, is to be obtained for the reconstruction of certain sectional images by means of a probe based on ultrasonic wave information, each single voxel inside the test body has to be scanned in different transmission cycles. A major measuring and evaluation effort which is not carried out with conventional emitter array technology.

LIST OF REFERENCES 1 emitter array probe
2 cable
3 amplifier
4 analog/digital transducer
5 time-delay element
6 digital adder
7 B-image reconstruction unit
8 ultrasonic transducer
9 test body surface

What is claimed is:

1. A method for non-destructive inspection of a test body using ultrasound, in which at least one ultrasonic transducer couples ultrasonic waves into the test body and ultrasonic waves reflected inside the test body are received by ultrasonic transducers and converted into ultrasonic signals, which form a basis for non-destructive inspection, comprising:

providing n distributed ultrasonic transducers disposed in an array on a surface of the test body and activating of at least one group of i of the n ultrasonic transducers so that i ultrasonic wave fronts which are coupled into the test body are superimposed to form a wave front propagating substantially uniformly spatially distributed inside the test body;

receiving of the ultrasonic waves reflected inside the test body with m ultrasonic transducers provided on the surface of the test body and generating m ultrasonic time signals containing time-resolved amplitude information;

storing the m ultrasonic time signals; and reconstructing a 3-dimensional volumetric image, a 2-dimensional ultrasonic sectional image through the test body or an A-image comprising a 1-dimensional time-resolved and locally resolved ultrasonic echo signal along a given irradiation angle solely using at least one part of the m ultrasonic time signals; and wherein $3 \leq i \leq n$ and the i ultrasonic transducers are disposed on the surface of the test body and excited in a time-delayed manner with transmission impulses so that a wave front propagating cylindrically or spherically from the i ultrasonic transducers forms inside the test body.

2. A method according to claim 1, wherein:

ultrasonic time signals received by the ultrasonic transducers are detected by consideration of a duration from a time of emission and a time of reception at each of the ultrasonic transducers so that a volume of the test body is subdivided into single spatial points, each comprising a voxel, to which at least one part of the ultrasonic echo signals is assigned corresponding to a value of the voxel.

3. A method according to claim 1, wherein receiving ultrasonic waves reflected inside the test body with a sampling phased array.

4. A method according to claim 3, wherein providing emission of ultrasonic waves by activating at least one ultrasonic transducer to provide pulses in a single transmission cycle.

5. A method according to claim 1, comprising providing emission of ultrasonic waves by activating at least one ultrasonic transducer to provide pulses in a single transmission cycle.

6. A method for non-destructive inspection of a test body using ultrasound, in which at least one ultrasonic transducer couples ultrasonic waves into the test body and ultrasonic waves reflected inside the test body are received by ultrasonic transducers and converted into ultrasonic signals, which form a basis for non-destructive inspection, comprising:

providing n distributed ultrasonic transducers disposed in an array on a surface of the test body and activating of at least one group of i of the n ultrasonic transducers so that i ultrasonic wave fronts which are coupled into the test body are superimposed to form a wave front propagating substantially uniformly spatially distributed inside the test body;

receiving of the ultrasonic waves reflected inside the test body with m ultrasonic transducers provided on the surface of the test body and generating m ultrasonic time signals containing time-resolved amplitude information;

storing the m ultrasonic time signals; and reconstructing a 3-dimensional volumetric image, a 2-dimensional ultrasonic sectional image through the test body or an A-image comprising a 1-dimensional time-resolved and locally resolved ultrasonic echo signal along a given irradiation angle solely using at least one part of the m ultrasonic time signals; and wherein ultrasonic time signals received by the ultrasonic transducers are detected, by consideration of a duration from a time of emission and a time of reception at each of the single ultrasonic transducers so that a volume of the test body is subdivided into single spatial points, each comprising a voxel, to which at least one part of the ultrasonic echo signals is assigned corresponding to value of the voxel.

7. A method according to claim 6 comprising:
reconstructing a volumetric image for a volume region by selecting the sector image for a sectional plane or the A-image of a irradiation angle through the test body and selecting a value of each voxel lying in a volumetric region, in the sectional plane or along the irradiation angle.

8. A method according to claim 7, wherein
receiving ultrasonic waves reflected inside the test body with a sampling phased array.

9. A method according to claim 7, wherein
providing emission of ultrasonic waves by activating at least one ultrasonic transducer to provide pulses in a single transmission cycle.

10. A method according to claim 6, wherein
providing emission of ultrasonic waves by activating at least one ultrasonic transducer to provide pulses in a single transmission cycle.

11. A method according to claim 6, wherein
receiving ultrasonic waves reflected inside the test body with a sampling phased array.

12. A method according to claim 11, wherein
providing emission of ultrasonic waves by activating at least one ultrasonic transducer to provide pulses in a single transmission cycle.

* * * * *